United States Patent [19]

Heinerman et al.

[11] 4,417,090

[45] Nov. 22, 1983

[54] PROCESS FOR THE ISOMERIZATION OF PARAFFINS

[75] Inventors: Jacobus J. L. Heinerman; Martin F. M. Post, both of Amsterdam, Netherlands

[73] Assignee: Shell Oil Company, Houston, Tex.

[21] Appl. No.: 430,470

[22] Filed: Sep. 30, 1982

[30] Foreign Application Priority Data

Nov. 2, 1981 [NL] Netherlands ......................... 8104950

[51] Int. Cl.$^3$ ........................... C07C 5/24; C07C 5/30
[52] U.S. Cl. .................................... 585/739; 208/135; 502/80; 502/259
[58] Field of Search ....................... 208/135; 585/739; 252/449, 455 Z

[56] References Cited

U.S. PATENT DOCUMENTS 3,766,292 10/1973 Wall et al. .
4,022,684 5/1977 Black et al. .

OTHER PUBLICATIONS

Swift et al., Ind. Eng. Chem. Prod. Res. Develop., 13(2), 106–109, (1974).
Wright et al., J. Catalysis, 25, 65–80, (1972).

Primary Examiner—Curtis R. Davis
Assistant Examiner—A. Pal
Attorney, Agent, or Firm—John M. Duncan

[57] ABSTRACT

A process for hydroisomerization of $C_4$–$C_7$ paraffins with a nickel and/or cobalt synthetic mica-montmorillonite catalyst which has been pretreated with hydrogen at a temperature of at least 400° C.

10 Claims, No Drawings

PROCESS FOR THE ISOMERIZATION OF PARAFFINS

BACKGROUND OF THE INVENTION

The invention relates to a process for the isomerization of paraffins.

For use as gasoline component highly branched paraffins are more suitable than unbranched or moderately branched paraffins having the same number of carbon atoms, since the former have a higher octane number.

For these reasons processes have been developed for the isomerization of paraffins with a lower degree of branching into paraffins with a higher degree of branching. An isomerization treatment of this type can be carried out, for example, by contacting the paraffins to be isomerized with a catalyst in the presence of hydrogen at elevated temperature and pressure, which catalyst contains a layered crystalline aluminosilicate and one or more catalytically active metals or metal compounds such as cobalt, nickel, platinum and palladium. See, for example, H. E. Swift, et al in Ind. ENg. Chem. Prod. Res. Develop., 13 (1974) No. 2, pp. 106–109, where the catalyst is pretreated (reduced) with hydrogen at a temperature of 650° F. (343° C.) before use in a hydroisomerization process.

In view of operational economy it is attractive to use catalysts containing no noble metals. The conversion so far obtained of the paraffins to be isomerized with the use of catalysts of the above type containing no platinum or palladium, however, is not entirely satisfactory, and moreover, the cracking activity of a catalyst of this type is higher than desirable.

It has now been found that the above-mentioned drawbacks do not occur if the catalyst used is a layered metal silicate containing as metals, in addition to aluminum, exclusively nickel and/or cobalt, which layered metal silicate has been treated with hydrogen at a temperature of at least 400° C. before it is used as isomerization catalyst.

SUMMARY OF THE INVENTION

A process is disclosed for the isomerization of paraffins, wherein one or more paraffins containing 4–7 carbon atoms is/are contacted with a catalyst in the presence of hydrogen at a temperature between 150° and 330° C., which catalyst has been prepared by treating an at least partly crystalline metal silicate having a space lattice largely consisting of a triplex structure containing in the central layer octahedrally co-ordinated aluminum entirely or partly substituted by nickel and/or cobalt, and in the two outer layers tetrahedrally co-ordinated silicon partly substituted by aluminum, with hydrogen at a temperature of at least 400° C.

DESCRIPTION OF PREFERRED EMBODIMENTS

Especially suitable catalysts for the process according to the invention consist of or contain a metal silicate at least partly consisting of synthetic mica-montmorillonite in which aluminum is partly substituted by nickel and/or cobalt. Synthetic mica-montmorillonite is described by A. C. Wright et al in J. of Catalysis 25 (1972), pp 65–80.

Catalysts in which the aluminum is partly substituted exclusively by nickel, are preferably used in the present process. The quantity of nickel in the catalyst is preferably at least 20% by weight, in particular at least 25% by weight, both percentages based on the total catalyst.

The catalysts used in the process according to the invention are preferably prepared via a hydrothermal synthesis route.

A metal silicate consisting of synthetic mica-montmorillonite, in which aluminum is partly substituted by nickel (abbreviated: NI-SMM), can suitably be prepared by entirely or largely substituting the sodium ions of a water-dispersed sodium silicate by protons by means of an ion exchanger in the H-form, and subsequently adding a nickel salt, an aluminum alcoholate, ammonia and, if desired, ammonium fluoride. The resulting slurry is partly evaporated and the gel obtained in subsequently heated to 250°–350° C. in an autoclave for several hours. The product obtained after filtration is dried and calcined at 400°–600° C. for several hours.

Ni-SMM can also suitably be prepared by adding a nickel salt and ammonium fluoride to appropriate silica-alumina dispersed in a small quantity of water and, if desired, partly evaporating the resulting slurry and subsequently introducing it into an autoclave for further treatment in the same manner as described in the former preparation method.

The nickel-substituted metal silicate prepared by one of the above methods is treated with hydrogen at a temperature of at least 400° C., in order to obtain a catalyst for the isomerization of paraffins according to the present process.

The metal silicate is preferably treated with hydrogen at a temperature between 400° and 550° C., in particular between 440° and 500° C., and at least atmospheric pressure, for at least several hours, in order to obtain a catalyst with optimum properties. The treatment with hydrogen can suitably take place as pretreatment in the reactor in which the isomerization is carried out.

It has surprisingly been found that in isomerization treatments of paraffins with 4–7 carbon atoms in the presence of hydrogen the conversion is substantially higher (while maintaining a high selectivity, usually higher than 95%) when using a catalyst according to the invention prepared by treating with hydrogen at a temperature of at least 400° C. the above-mentioned metal silicate than with the use of a catalyst prepared by treating with hydrogen the same metal silicate at a lower temperature.

The starting material used in the process according to the invention consists of one or more paraffins with 4–7 carbon atoms, preferably mainly or entirely or normal pentane or normal hexane or mixtures thereof. "Tops" obtained in the atmospheric distilliation of petroleum are very suitably used as starting material.

The intention is that in the process according to the invention the greatest possible quantity of the paraffins present in the feed is converted into isomers of said paraffins with a higher degree of branching, whereas their degree of cracking into products with a lower number of carbon atoms than the molecules in the feed must be kept to a minimum.

Suitable conditions for carrying out the process according to the invention are:
a temperature between 150° and 330° C., preferably between 200° and 300° C.;
a space velocity between 0.5 and 10 kg of paraffin/kg of catalyst/hour;
a hydrogen: paraffin molar ratio in the range from 1:1 to 25:1 and a total pressure between 1 and 70 bar.
Very suitable conditions are:

a temperature between 220° and 280° C.;
a space velocity between 1 and 5 kg of paraffin/kg of catalyst/hour;
a hydrogen; paraffin molar ratio in the range from 1:1 to 15:1 and
a total pressure between 20 and 50 bar.

In most cases it is not necessary to use pure hydrogen, and hydrogen-containing gases are also suitable. A hydrogen-rich gas obtained in the catalytic reforming of hydrocarbon mixtures, such as naphtha, is very suitable.

EXAMPLE

Preparation of catalyst A 350 g of sodium water glass containing 28% by weight of $SiO_2$, are dispersed in 2.5 l of deionized water and subsequently treated three times with 500 ml (400 g) of Amberlite IR120-H ion exchanger in the H-form for 20 minutes. Subsequently, a solution of 380 g of nickel acetate. 4 aq in 1200 ml of water, 235 g of ground aluminum isopropylate, 7.5 g of ammonium fluoride and 50 ml of ammonia (25% by weight of $NH_3$) are added to the liquid with stirring. The resulting slurry is evaporated with stirring for 24 hours to a volume of 2.8 l. A quantity of 275 g of the slurry is heated to 300° C. in an autoclave and this temperature is maintained for 48 hours. The autoclave is subsequently cooled to room temperature and the product is filtered and washed with water until a clear filtrate is obtained. The product is dried at 120° C. and subsequently calcined at 500° C. for 17 hours. The yield is 22.0 g of material containing 27.1% by weight of nickel. The resulting Ni-SMM is treated with hydrogen in the isomerization reactor for 16 hours at a pressure of 1 bar and a temperature of 450° C.

Preparation of catalyst B 119.0 g of a silica-alumina containing 21.6% by weight of $Al_2O_3$ and 13.8% by weight of water, based on the total weight, are dispersed in 220 g of deionized water. A quantity of 195.3 g of nickel acetate. 4 aq is added with stirring to the resulting slurry which is subsequently evaporated to a volume of 330 ml. After the addition of 10.38 g of ammonium fluoride with stirring, the slurry is heated to 295° C. in a 0.5-liter autoclave in 3 hours and maintained at said temperature for 64 hours. The autoclave is subsequently cooled to room temperature in about 5 hours and the resulting product is filtered, washed and dried at 120° C. The yield is 162 g of dry material exhibiting the Ni-SMM X-ray diffraction pattern. The Ni-SMM is calcined at 540° C. for 1 hour and is subsequently treated with hydrogen in the isomerization reactor for 16 hours at a pressure of 1 bar and a temperature of 450° C.

Hydroisomerization of pentane

Pentane hydroisomerization tests are carried out in a microflow tubular reactor with a length of 35 cm and an inside diameter of 1 cm, containing 2 g of catalyst particles (mesh 0.18–0.59 mm). If the treatment with hydrogen at 450° C. of Ni-SMM has taken place in the tubular reactor, the temperature therein is reduced to 250° C. both with the use of catalyst A and of catalyst B and the predried normal pentane feed is subsequently passed over the catalyst together with pure hydrogen.

The reaction conditions during the hydroisomerization treatment are:

| temperature | 250° C. |
| total pressure | 30 bar |
| hydrogen/pentane molar ratio | 1.25 |
| space velocity | 2 g of pentane/ g catalyst/h |

The product stream is continuously analyzed by means of gas-liquid chromatography.

In the table below "Conversion, %, i-$C_5$% and Cracking, %" are respectively, the weight percentages of converted pentane, isomerized pentane and resulting product with less than 5 C-atoms; all percentages are based on pentane feed.

The catalysts C and D are obtained by treating Ni-SMM, prepared in the same manner as for catalysts A and B, respectively, with hydrogen at a temperature of 350° C. and a pressure of 1 bar. Tests 1 and 2 state the results of tests according to the invention, tests 3 and 4 are comparative tests not according to the invention.

TABLE

| Test No. | Catalyst | Temp. pretreatment with $H_2$ (°C.) | % by wt. of Ni in cat | Conversion, % | i-$C_5$ % | Cracking % | Selectivity, % |
|---|---|---|---|---|---|---|---|
| 1 | A | 450 | 27.1 | 59 | 59 | <0.5 | >99.5 |
| 2 | B | 450 | 26.2 | 60 | 58 | 2 | 97 |
| 3 | C | 350 | 27.1 | 38 | 38 | <0.5 | >99.5 |
| 4 | D | 350 | 26.2 | 40 | 39 | 1 | 98 |

Treatment of Ni-SMM with hydrogen at 450° C. results in substantially higher conversion and i-$C_5$ percentages, compared with treatment with hydrogen at 350° C., which has been employed heretofore in hydroisomerization processes.

What is claimed is:

1. A process for the isomerization of paraffins, wherein one or more paraffins containing 4–7 carbon atoms is/are contacted with a catalyst in the presence of hydrogen, at a temperature between 150° and 330° C., which catalyst has been prepared by treating an at least partly crystalline metal silicate having a space lattice largely consisting of a triplex structure, containing in the central layer octahedral co-ordinated aluminum entirely or partly substituted by nickel and/or cobalt, and in the two outer layers tetrahedral co-ordinated silicon partly substituted by aluminum, with hydrogen at a temperature of at least 400° C.

2. The process of claim 1, wherein the metal silicate consists at least partly of synthetic mica-montmorillonite, in which aluminum is partly substituted by nickel and/or cobalt.

3. The process of claim 1 or 2, characterized in that aluminum is partly substituted exclusively by nickel.

4. The process of claim 3, wherein the catalyst contains at least 20% by weight of nickel, based on the total catalyst.

5. The process of claim 4, wherein the catalyst contains at least 25% by weight of nickel, based on the total catalyst.

6. The process of claim 4, wherein the metal silicate has been treated with hydrogen at a temperature between 400° and 550° C.

7. The process of claim 6, wherein the metal silicate has been treated with hydrogen at a temperature between 440° and 500° C.

8. The process of claim 1, wherein the paraffins containing 4–7 atoms mainly or entirely consist of normal pentane and/or normal hexane.

9. The process of claim 1, wherein the isomerization is carried out at a temperature between 200° and 300° C., a space velocity between 0.5 and 10 kg of paraffin/kg of catalyst/h; a hydrogen/paraffin molar ratio in the range from 1:1 to 25:1, and a total pressure between 1 and 70 bar.

10. The process of claim 9, wherein the isomerization is carried out at a temperature between 220° and 280° C., a space velocity between 1 and 5 kg of paraffin/kg of catalyst/h, a hydrogen/paraffin molar ratio in the range from 1:1 to 15:1 and a total pressure between 20 and 50 bar.

* * * * *